(12) United States Patent
Roy et al.

(10) Patent No.: US 8,968,316 B2
(45) Date of Patent: Mar. 3, 2015

(54) APPARATUS WITH MULTIPLE CHANNEL SELECTIVE CUTTING

(75) Inventors: Jeffrey M. Roy, Boulder, CO (US); Rebecca Coulson, Lyons, CO (US)

(73) Assignee: Covidien LP, Mansfield, MA (US)

( * ) Notice: Subject to any disclaimer, the term of this patent is extended or adjusted under 35 U.S.C. 154(b) by 1050 days.

(21) Appl. No.: 13/030,231

(22) Filed: Feb. 18, 2011

(65) Prior Publication Data
US 2012/0215219 A1     Aug. 23, 2012

(51) Int. Cl.
| | |
|---|---|
| *A61B 18/14* | (2006.01) |
| *A61B 17/295* | (2006.01) |
| *A61B 17/29* | (2006.01) |
| *A61B 18/00* | (2006.01) |
| *A61B 19/00* | (2006.01) |

(52) U.S. Cl.
CPC ........... *A61B 17/295* (2013.01); *A61B 18/1445* (2013.01); *A61B 2017/2925* (2013.01); *A61B 2017/2929* (2013.01); *A61B 2018/00601* (2013.01); *A61B 2018/1455* (2013.01); *A61B 2019/304* (2013.01)
USPC .................................. 606/52; 606/51; 606/46

(58) Field of Classification Search
USPC ...................... 606/45–52, 205–207
See application file for complete search history.

(56) References Cited

U.S. PATENT DOCUMENTS

| | | | |
|---|---|---|---|
| D249,549 S | 9/1978 | Pike | |
| D263,020 S | 2/1982 | Rau, III | |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| D384,413 S | 9/1997 | Zlock et al. | |
| 5,674,220 A * | 10/1997 | Fox et al. ........................ | 606/51 |
| 5,797,938 A | 8/1998 | Paraschac et al. | |
| D402,028 S | 12/1998 | Grimm et al. | |
| 5,960,544 A | 10/1999 | Beyers | |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

European Search Report for European Application No. 12155728.4 dated Jun. 28, 2012.

(Continued)

*Primary Examiner* — Michael Peffley (57) ABSTRACT

A forceps includes an end effector assembly and one or more cutting blades. The end effector assembly defines a longitudinal axis and has a pair of jaw members selectively positionable relative to one another about a pivot. One or more of the jaw members includes an electrically conductive tissue engaging surface adapted to connect to an electrosurgical energy source. One or more of the jaw members includes two or more blade channels defined therein and extending therealong. The one or more cutting blades are selectively movable within one or more of the two or more blade channels.

20 Claims, 6 Drawing Sheets

(56) References Cited

U.S. PATENT DOCUMENTS

| | | |
|---|---|---|
| D416,089 S | 11/1999 | Barton et al. |
| D424,694 S | 5/2000 | Tetzlaff et al. |
| D425,201 S | 5/2000 | Tetzlaff et al. |
| D449,886 S | 10/2001 | Tetzlaff et al. |
| D454,951 S | 3/2002 | Bon |
| D457,958 S | 5/2002 | Dycus et al. |
| D457,959 S | 5/2002 | Tetzlaff et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al |
| D545,432 S | 6/2007 | Watanabe |
| D547,154 S | 7/2007 | Lee et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 2004/0122423 A1 | 6/2004 | Dycus et al. |
| 2006/0189981 A1 | 8/2006 | Dycus et al. |
| 2008/0021450 A1 | 1/2008 | Couture |
| 2009/0012520 A1 | 1/2009 | Hixon et al. |
| 2011/0009864 A1 | 1/2011 | Bucciaglia et al. |
| 2011/0054469 A1 | 3/2011 | Kappus et al. |
| 2011/0060334 A1 | 3/2011 | Brandt et al. |
| 2011/0087221 A1 | 4/2011 | Siebrecht et al. |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 19738457 | 1/2009 |
| DE | 10 2008 018406 | 7/2009 |
| EP | 1159926 | 12/2001 |
| JP | 61-501068 | 9/1984 |
| JP | 65-502328 | 3/1992 |
| JP | 5-5106 | 1/1993 |
| JP | 5-40112 | 2/1993 |
| JP | 6-285078 | 10/1994 |
| JP | 6-511401 | 12/1994 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 10-24051 | 1/1998 |
| JP | 11-070124 | 5/1998 |
| JP | 2000-102545 | 9/1998 |
| JP | 11-169381 | 6/1999 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| JP | 2001-190564 | 7/2001 |
| SU | 401367 | 11/1974 |
| WO | WO 00/36986 | 6/2000 |
| WO | WO 01/15614 | 3/2001 |
| WO | WO 01/54604 | 8/2001 |
| WO | WO 2005/110264 | 11/2005 |

OTHER PUBLICATIONS

An extended European Search Report corresponding to European Application No. 12 15 5728.4, completed on Jun. 28, 2012 and mailed on Jul. 4, 2012; 4 pages.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/576,380, filed Oct. 9, 2009, Wayne Siebrecht.
U.S. Appl. No. 12/607,191, filed Oct. 28, 2009, William H. Nau, Jr.
U.S. Appl. No. 12/619,100, filed Nov. 16, 2009, Jennifer S. Harper.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Norner.
U.S. Appl. No. 12/770,369, filed Apr. 29, 2010, Glenn A. Horner.
U.S. Appl. No. 12/770,380, filed Apr. 29, 2010, Glenn A. Horner.
U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.

(56) References Cited

OTHER PUBLICATIONS

U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/004,984, filed Jan. 12, 2011, David M. Garrison.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/048,679, filed Mar. 15, 2011, Paul Guerra.
U.S. Appl. No. 13/075,847, filed Mar. 30, 2011, Gary M. Couture.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, The Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands, Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. " Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.

(56) References Cited

OTHER PUBLICATIONS

Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Intl Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Intl Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181969.6 dated Feb. 4, 2011.
Int'l Search Report EP 10 191320.0 dated Feb. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

APPARATUS WITH MULTIPLE CHANNEL SELECTIVE CUTTING

BACKGROUND

1. Technical Field

The present disclosure relates to surgical instruments. More particularly, the present disclosure relates to a surgical apparatus with multiple knife channels for facilitating the selective cutting of tissue.

2. Background of Related Art

Electrosurgical apparatuses (e.g., electrosurgical forceps) are well known in the medical arts and typically include a handle, a shaft and an end effector assembly operatively coupled to a distal end of the shaft that is configured to manipulate tissue (e.g., grasp and seal tissue). Electrosurgical forceps utilize both mechanical clamping action and electrical energy to effect hemostasis by heating the tissue and blood vessels to coagulate, cauterize, fuse, seal, cut, desiccate, and/or fulgurate tissue.

As an alternative to open electrosurgical forceps for use with open surgical procedures, many modern surgeons use endoscopes and endoscopic electrosurgical apparatuses (e.g., endoscopic or laparoscopic forceps) for remotely accessing organs through smaller, puncture-like incisions. As a direct result thereof, patients tend to benefit from less scarring, less pain, and reduced healing time. Typically, the endoscopic forceps is inserted into the patient through one or more various types of cannulas or access ports (typically having an opening that ranges from about five millimeters to about fifteen millimeters) that has been made with a trocar; as can be appreciated, smaller cannulas are usually preferred.

An endoscopic forceps that is configured for use with small cannulas (e.g., cannulas less than five millimeters) may present design challenges for a manufacturer of endoscopic instruments.

SUMMARY

Accordingly, the present disclosure is directed to a forceps including one or more shafts that include an end effector assembly at a distal end thereof and one or more cutting blades. The end effector assembly has a pair of jaw members selectively positionable relative to one another about a pivot. One of the jaw members includes an electrically conductive tissue engaging surface adapted to connect to an electrosurgical energy source. One or more of the jaw members includes two or more blade channels defined therein and extending therealong. One or more of the cutting blades are selectively positionable and translatable within one or more of the two or more blade channels.

One or more of the blade channels may be positioned offset from a longitudinal axis defined through the center of the end effector assembly. A wide seal zone is defined along the tissue engaging surface adjacent the one or more offset blade channels. One or more of the blade channels may be longitudinally aligned with a longitudinal axis defined through the center of the end effector assembly. The forceps may include two or more cutting blades that are sequentially or simultaneously deployable. The forceps may include a channel selection assembly operable to selectively position the one or more cutting blades relative to one or more blade channels. The channel selection assembly includes an actuator having a moving assembly operably coupled thereto that positions the one or more cutting blades relative to one or more blade channels upon actuation of the actuator. The forceps may include two or more cutting blades and a moving assembly. Each cutting blade may be aligned with a corresponding blade channel or movable to a position in alignment therewith.

The moving assembly includes one or more blade movers that are movable between extended and retracted positions. The blade movers position the respective cutting blades relative to the blade channels as the blade movers move between the extended and retracted positions. When the blade movers are in the extended position, the blade movers are positioned to engage corresponding cutting blades so that the cutting blades are positioned in alignment with blade channels. One or more of the blade channels may be positioned offset from the longitudinal axis.

In some embodiments, the blade movers bend the cutting blades into alignment with the blade channels when the blade movers move between the retracted and extended positions. In one embodiment, the blade movers move the entirety of the cutting blades laterally into alignment with corresponding blade channels as the blade movers move between the extended and retracted positions.

In some embodiments, the moving assembly includes two or more blade movers wherein each blade mover moves between extended and retracted positions. The two or more blade movers may move in reciprocal relation relative to one another.

In some embodiments, the moving assembly includes a pusher, a pusher mover, and an actuator. The pusher mover aligns the pusher with the cutting blades upon actuation of the actuator. Axial translation of the pusher moves the cutting blades along the blade channels.

According to one aspect, the present disclosure is directed to a method of cutting tissue grasped between the jaw members of an end effector of a forceps. The forceps includes one or more cutting blades. The end effector includes two or more blade channels defined therein and extending therealong. The method involves positioning the cutting blades relative to one of the two or more blade channels, moving the cutting blades through the blade channels, and cutting tissue with the cutting blades along the blade channels.

According to another aspect, a method of cutting tissue with a forceps includes the step of providing a forceps including one or more shafts that includes an end effector assembly at a distal end thereof. The end effector assembly defines a longitudinal axis through the center thereof and has a pair of jaw members selectively positionable relative to one another about a pivot. One or more of the jaw members includes an electrically conductive tissue engaging surface adapted to connect to an electrosurgical energy source and includes two or more blade channels defined therein and extending therealong. The forceps includes one or more cutting blades selectively positionable and translatable within one or more of the two or more blade channels. The method also includes: grasping tissue; engaging the pair of jaw members and supplying energy to create a tissue seal; positioning the one or more cutting blades in one of the two or more blade channels; and advancing the one or more cutting blades to cut the tissue along the tissue seal to form two seal ends. One step may involve creating a wide seal end and a narrow seal end by transecting tissue offset relative to the longitudinal axis with the one or more cutting blades.

BRIEF DESCRIPTION OF THE DRAWINGS

Various embodiments of the present disclosure are described hereinbelow with references to the drawings, wherein.

DETAILED DESCRIPTION OF EMBODIMENTS

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As noted above, it may prove useful to provide an electrosurgical apparatus that is suitable for use with various access ports, including but not limited to those that are greater than and/or less than five millimeters. With this purpose in mind, the present disclosure includes an electrosurgical forceps that includes a drive assembly operatively coupled to one or more jaw members associated with the end effector assembly of the electrosurgical forceps. The drive assembly is configured to move the jaws from an open to a closed configuration that forms a closed loop electrical circuit such that a desired tissue effect (e.g., tissue seal) may be achieved.

Figure 1:
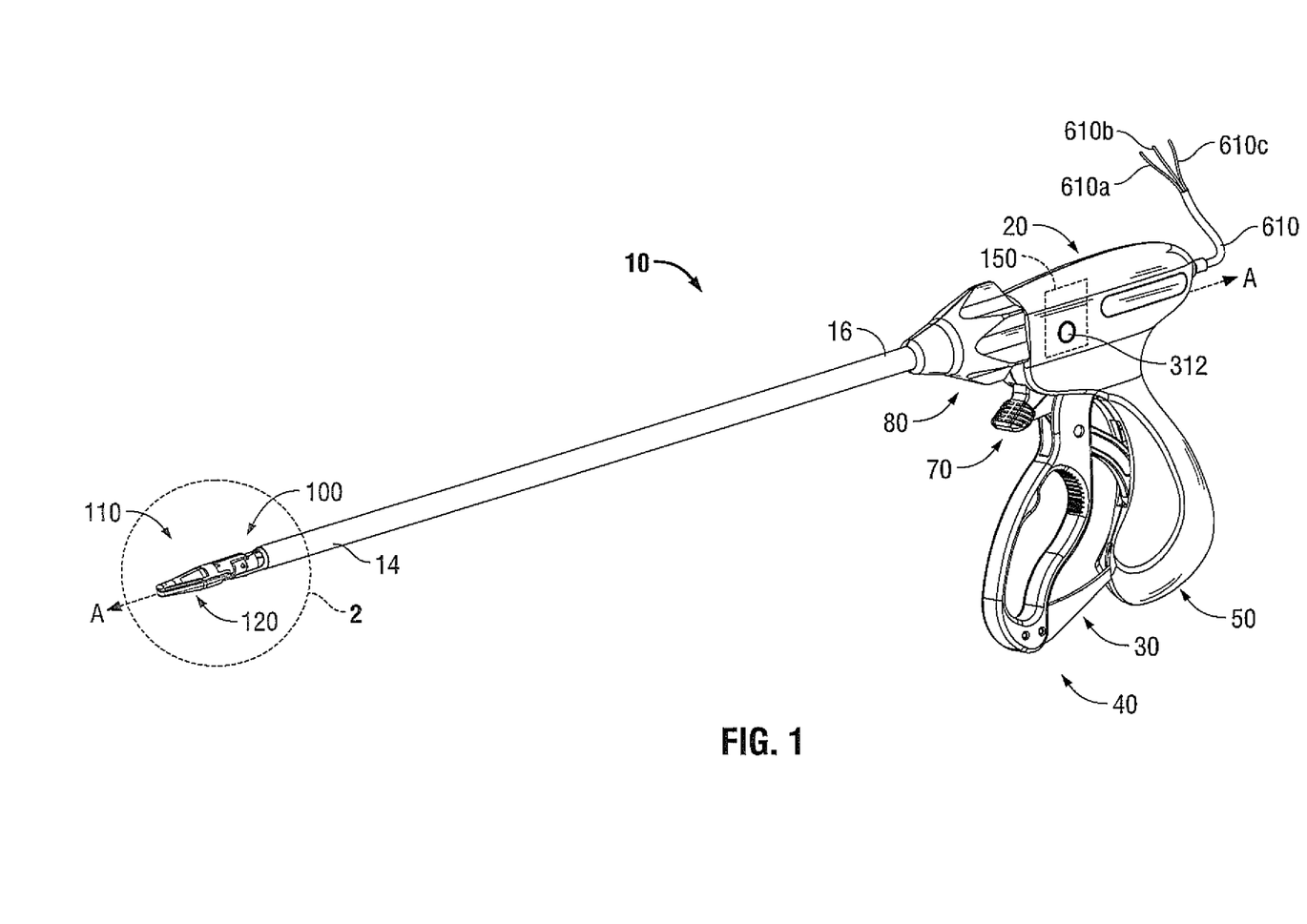
FIG. 1 is a right, perspective view of an example endoscopic bipolar forceps showing a housing, a shaft, and an end effector assembly.

Turning now to FIG. 1, an embodiment of an endoscopic bipolar forceps 10 is shown for use with various surgical procedures and generally includes a housing 20, a handle assembly 30, a rotating assembly 80, a trigger assembly 70, and an end effector assembly 100 that mutually cooperate to grasp, seal, and divide tubular vessels and vascular tissue. Although the majority of the figure drawings depict a bipolar forceps 10 for use in connection with endoscopic surgical procedures, the present disclosure may be used for more traditional open surgical procedures. For the purposes herein, the forceps 10 is described in terms of a laparoscopic instrument; however, it is contemplated that an open version of the forceps may also include the same or similar operating components and features as described below.

Forceps 10 includes a shaft 12 that has a distal end 14 configured to mechanically engage the end effector assembly 100 and a proximal end 16 that mechanically engages the housing 20. In the drawings and in the descriptions that follow, the term "proximal", as is traditional, will refer to the end of the forceps 10 that is closer to the user, while the term "distal" will refer to the end that is farther from the user.

Forceps 10 includes an electrosurgical cable 610 that connects the forceps 10 to a source of electrosurgical energy, e.g., a generator (not shown). One such source of electrosurgical energy is described in commonly-owned U.S. Pat. No. 6,033,399 entitled "ELECTROSURGICAL GENERATOR WITH ADAPTIVE POWER CONTROL." Cable 610 is internally divided into cable leads 610a, 610b, and 610c, which are designed to transmit electrical potentials through their respective feed paths through the forceps 10 to the end effector assembly 100. In some embodiments, the forceps 10 may also be battery-powered.

A more detailed description of handle assembly 30, movable handle 40, rotating assembly 80, and electrosurgical cable 610 (including line-feed configurations and/or connections) is described in U.S. Pat. No. 7,101,371, entitled "VESSEL SEALER AND DIVIDER" by Dycus et al.

Handle assembly 30 includes a fixed handle 50 and a movable handle 40. Fixed handle 50 is integrally associated with housing 20 and handle 40 is movable relative to fixed handle 50 as explained in more detail below with respect to the operation of the forceps 10. Rotating assembly 80 is operatively connected to the housing 20 and is rotatable in either direction about a longitudinal axis "A-A" (See FIG. 1).

As mentioned above, end effector assembly 100 is attached at the distal end 14 of shaft 12 and includes a pair of opposing jaw members 110 and 120. Movable handle 40 of handle assembly 30 is operatively connected to a drive assembly 150 (shown in phantom) that, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween. With this purpose in mind, drive assembly 150 may include any suitable number of electrical connections, configurations, and/or components (e.g., resistors, capacitors, inductors, rheostats, etc.), mechanical connections, configurations, and/or components (e.g., gears, links, springs, rods, etc.), and/or electro-mechanical connections, configurations, and/or components such that forceps 10 may function as intended.

As shown best in FIGS. 1-5, the end effector assembly 100 includes opposing jaw members 110 and 120 that cooperate to effectively grasp tissue for sealing purposes. The end effector assembly 100 may be designed as a unilateral assembly, e.g., jaw member 120 is fixed relative to the shaft 12 and jaw member 110 pivots about a pivot pin 103 relative to jaw member 120 to grasp tissue, or as a bilateral assembly, e.g., jaw members 110 and 120 pivot about pivot pin 103 relative to each other to grasp tissue. In some embodiments and as will be discussed in further detail below, jaw members 110, 120 are operably coupled to each other via pivot pin 103 which allows jaw member 110 to pivot relative to stationary jaw member 120. In some embodiments, fixed jaw member 120 may be monolithically formed with shaft 12, e.g., stationary jaw member 120 may be defined by the distal end 14 of shaft 12.

Pivoting jaw member 110 may be formed from any suitable material, for example without limitation, metallic material such as aluminum and alloys thereof; plated brass, stainless steel, stainless steel alloys, beryllium copper, etc. In other embodiments, one or both jaw members 110 and 120 may be formed from material having malleable or flexible properties or, alternatively, one or both of jaw members 110 and 120 may be formed from a material having inflexible properties. In yet another embodiment, the distal end of the jaw 110 is configured to engage and/or grasp tissue prior to a middle portion and/or a proximal or "rear" end of the jaw 110, which is termed "tip-biased." More specifically, after the distal end of jaw member 110 engages tissue, the middle and/or proximal end of jaw member 110 are then caused to rotate inward toward the fixed jaw member 120 such that tissue may be grasped therebetween. The jaw member 110 operates to allow precision generation of pressure on tissue grasped between jaw members 110 and 120 for purposes of sealing the tissue, as will be discussed in more detail below.

Figure 2:
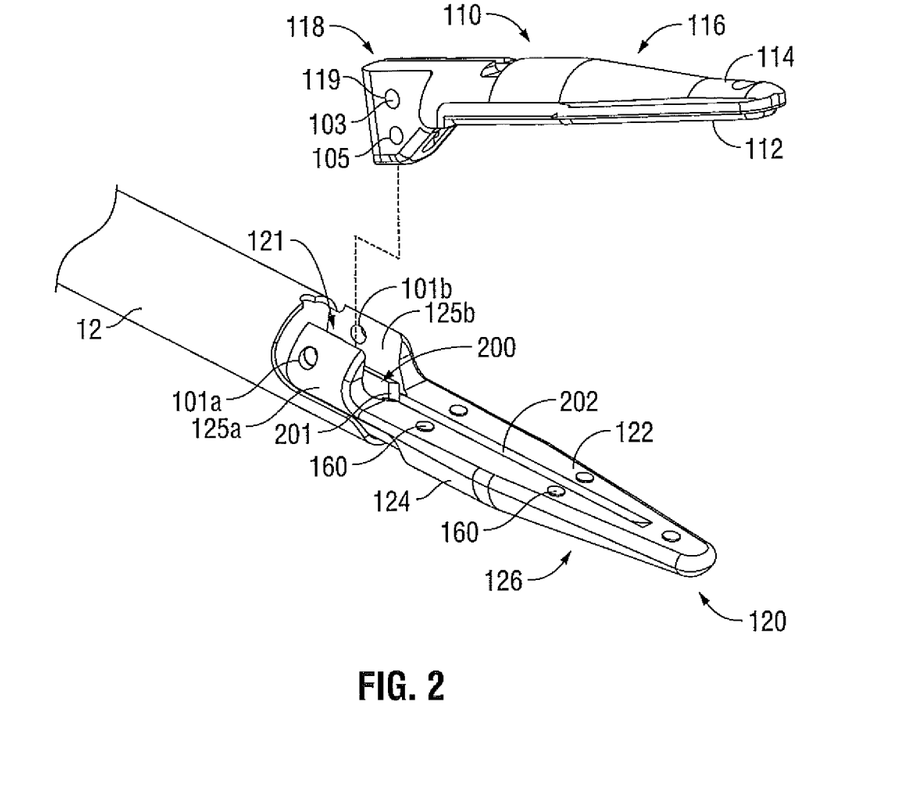
FIG. 2 is an enlarged, left perspective view, with parts separated, of the end effector assembly of FIG. 1.
Figure 3:
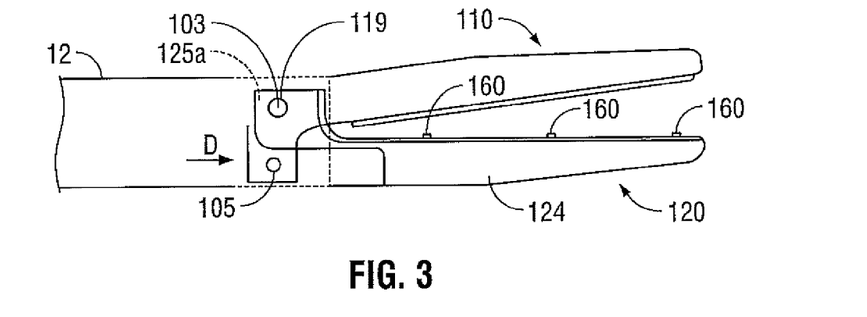
FIG. 3 is an enlarged, left side view of the end effector assembly of FIGS. 1-2 with jaw members of the end effector assembly being shown in an open configuration.

Referring now to FIG. 2, jaw member 110 includes a pivot flange 118 having a mechanical interface 105 disposed thereon. Mechanical interface 105 may be, without limitation, a link, a gear, a pin, a rod, any combination thereof, or any interface suitable to operably couple pivot flange 118 to drive assembly 150. Pivot flange 118 also includes a pin slot 119 that is configured to engage pivot pin 103 to allow jaw member 110 to rotate relative to jaw member 120. More particularly, jaw member 120 includes a pair of proximal, upwardly extending flanges 125a and 125b which define a cavity 121 configured to receive flange 118 of movable jaw member 110 therein. Each of the flanges 125a and 125b includes an aperture 101a and 101b, respectively, defined therethrough which secures pivot pin 103 on opposite sides of pivot mount 119 disposed within jaw member 110. As explained in further detail below, proximal movement of the drive assembly 150 engages mechanical interface 105 to pivot jaw member 110 to a closed position.

As best shown in FIGS. 1-4, mechanical interface 105 is operable by the drive assembly 150 such that drive assembly 150 urges mechanical interface 105 in the distal and proximal directions, as indicated by directional arrows "D" and "P", respectively. The pivoting jaw member 110 is actuated by the drive assembly 150 such that the pivoting jaw member 110 pivots about pivot pin 103 between open and closed positions. Pulling the mechanical interface 105 proximally closes the jaw members 110 and 120 about tissue grasped therebetween and pushing the mechanical interface 105 distally opens the jaw members 110 and 120 for grasping purposes. In another embodiment, pivot pin 103 is configured to slide within a cam slot to pivot jaw member 110 between open and closed positions.

As best shown in FIG. 2, jaw member 110 also includes a jaw housing 116 which has an insulative substrate or insulator 114 and an electrically conducive surface 112. Insulator 114 is configured to securely engage the electrically conductive sealing surface 112. This may be accomplished by stamping, by overmolding, by overmolding a stamped electrically conductive sealing plate and/or by overmolding a metal injection molded seal plate.

All of these manufacturing techniques produce jaw member 110 having an electrically conductive surface 112 which is substantially surrounded by an insulating substrate 114. The insulator 114, electrically conductive sealing surface 112 and the outer, non-conductive jaw housing 116 are configured to limit and/or reduce many of the known undesirable effects related to tissue sealing, e.g., flashover, thermal spread and stray current dissipation. In other embodiments, the jaw members 110 and 120 may be manufactured from a ceramic-like material and the electrically conductive surface(s) 112 are coated onto the ceramic-like jaw members 110 and 120.

Jaw member 120 includes similar elements to jaw member 110 such as jaw housing 126 having an insulator 124 and an electrically conductive sealing surface 122 that is configured to securely engage the insulator 124.

As best shown in FIG. 2, jaw member 120 may include a series of stop members 160 disposed on the inner facing surfaces of the electrically conductive sealing surface 122 to facilitate gripping and manipulation of tissue and to define a gap "G" (FIG. 11) between opposing jaw members 110 and 120 during sealing and cutting of tissue. In some embodiments, the gap distance between opposing sealing surfaces 112 and 122 during sealing ranges from about 0.001 inches to about 0.006 inches and, in other embodiments, between about 0.002 and about 0.003 inches. Pivoting jaw member 110 pivots about pivot pin 103 to the closed position such that conductive sealing surface 112 engages stop members 160. The flexible nature of jaw member 110 allows an operator to generate additional sealing pressure on tissue grasped between the jaw members 110 and 120. More specifically, once end effector assembly 100 is in the closed position and pivoting jaw member 110 is engaged with stop members 160, movable handle 40 may be squeezed relative to stationary handle 50 to utilize the flexibility of jaw member 110 to vary and/or generate additional closure pressure between jaw member 110 and stop members 160 for purposes of sealing tissue. The series of stop members 160 may be employed on one or both jaw members 110 and 120 depending upon a particular purpose or to achieve a desired result. A detailed discussion of stop members 160 as well as various manufacturing and assembling processes for attaching and/or affixing the stop members 160 to the electrically conductive sealing surfaces 112, 122 are described in U.S. Pat. No. 7,473,253 entitled "VESSEL SEALER AND DIVIDER WITH NON-CONDUCTIVE STOP MEMBERS" by Dycus et al.

Figure 4:
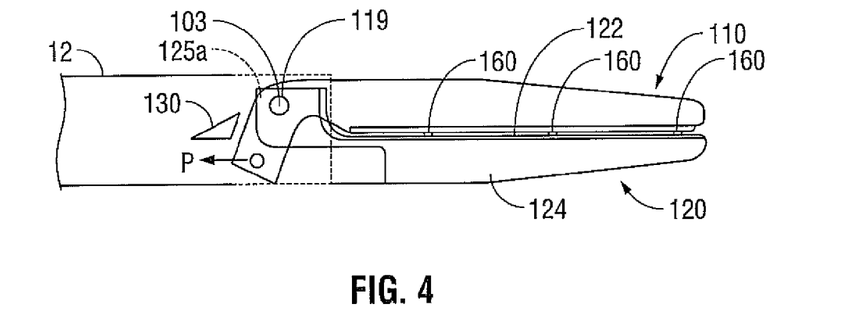
FIG. 4 is an enlarged, left side view of the end effector assembly of FIGS. 1-3 with the jaw members of the end effector assembly shown in a closed configuration.
Figure 5:
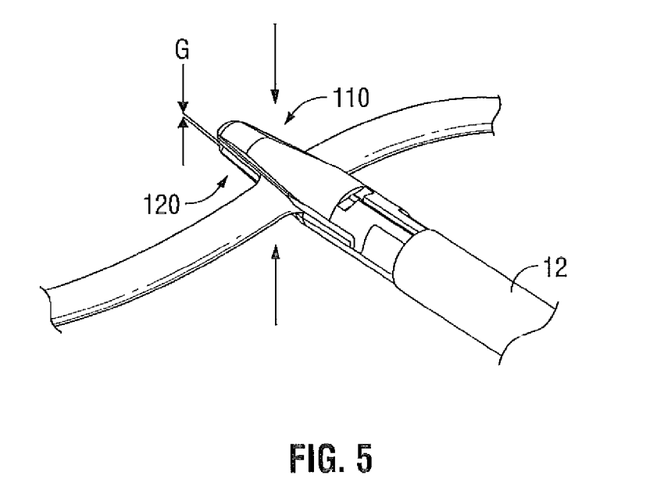
FIG. 5 is an enlarged, rear, perspective view of the end effectors shown grasping tissue.

As illustrated in FIG. 4, forceps 10 may include a camming member 130 disposed within shaft 12 and positioned to engage pivoting jaw member 110 at flange 118 when pivoting jaw member 110 is pivoted to the closed position. More specifically, as pivoting jaw member 110 pivots about pivot pin 103 from the open position to the closed position, e.g., in a clock-wise direction, camming member 130 cams a surface of flange 118 to prevent further pivoting of jaw member 110 about pivot pin 103 in the clock-wise direction. Once end effector assembly 100 is in the closed position, and camming member 130 is engaged with flange 118, movable handle 40 may be squeezed relative to stationary handle 50 to utilize the flexibility of jaw member 110 to vary and/or generate additional closure pressure between jaw members 110 and 120 and/or between jaw member 110 and stop members 160, as discussed hereinabove.

As the handle 40 is squeezed, the mechanical interface 105 is pulled proximally by the movement of drive assembly 150 to rotate flange 118 clock-wise which, in turn, pivots jaw member 110 about pivot pin 103 to the closed position.

The mechanical advantage realized from the jaw member 110, as discussed hereinabove, will enable the operator to impart a load on the drive assembly 150 by squeezing handle 40 (e.g., through use of an operably coupled torsion spring). The drive assembly's 150 load is converted to a torque about the jaw pivot 103. As a result, a specific closure force can be transmitted to the opposing jaw members 110 and 120. Alternatively or additionally, stationary jaw member 120 may be formed from material having malleable or flexible properties to provide a mechanical advantage. Further, the jaw members 110 and 120 may be opened, closed and rotated via rotating assembly 80 to manipulate tissue until sealing is desired. This enables the user to position and re-position the forceps 10 prior to activation and sealing.

Once jaws members 110 and 120 are fully compressed about the tissue, the forceps 10 are now ready for selective application of electrosurgical energy and subsequent separation of the tissue.

The mechanical advantage provided by the one or both of jaw members 110 and 120 facilitates and assures consistent, uniform and accurate closure pressure about tissue within the desired working pressure range of about 3 kg/cm$^2$ to about 16 kg/cm$^2$ or preferrably, about 7 kg/cm$^2$ to about 13 kg/cm$^2$. By controlling the intensity, frequency and duration of the electrosurgical energy applied to tissue, the operator can cauterize, coagulate/desiccate, seal and/or simply reduce or slow bleeding.

Referring again to FIG. 2, the end effector assembly 100 includes a knife assembly 200 (operably associated with the trigger assembly 70), that progressively and selectively divides tissue along a tissue plane in a precise manner to effectively divide the tissue. The knife assembly 200 includes a cutting blade 201 and a blade channel 202 extending along either one or both of the jaw members 110, 120. The cutting blade 201 is configured for selective translation within the blade channel 202.

Figures 6, 6A:
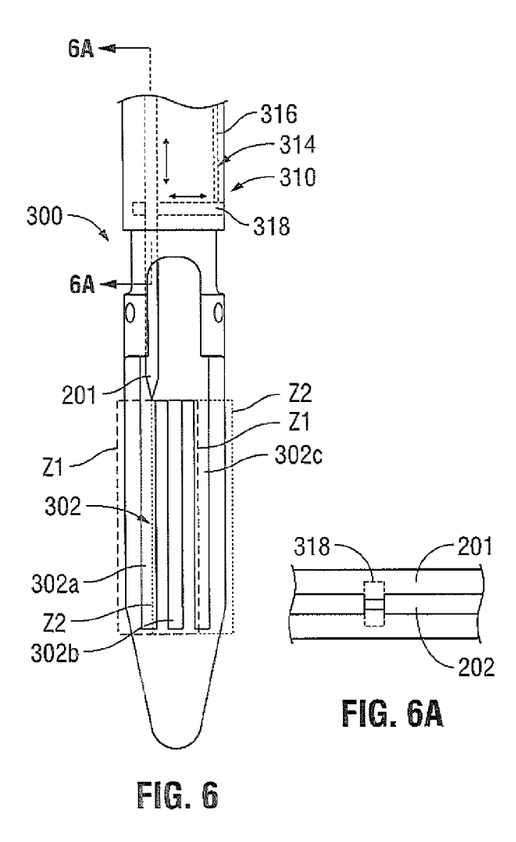
FIG. 6 is an enlarged, top plan view of the bottom jaw of one of the presently disclosed end effectors showing one embodiment of the presently disclosed knife assemblies in accordance with the present disclosure.
FIG. 6A is a partial, cross-sectional view of the indicated area of detail delineated in FIG. 6.

One embodiment of a knife assembly is referred to generally as 300 and is illustrated in FIG. 6. Knife assembly 300 is similar to knife assembly 200 and is described herein only to the extent necessary to describe the differences in construction and operation. The knife assembly 300 defines a plurality of blade channels 302, in particular, first, second, and third blade channels 302a, 302b, 302c, respectively. In the illustrated embodiment, the second blade channel 302b is aligned with the longitudinal axis and the first and third blade channels 302a and 302c are offset therefrom on opposed sides of second blade channel 302b. In this respect, wide seal zones "Z1" and "Z2" are defined along the tissue engaging surface adjacent the one or more offset blade channels 302a, 302c in the portion of the tissue engaging surface having the greater width. The cutting blade 201 is positioned to selectively translate through one or more of the plurality of blade channels 302 and may be sequentially deployable through one or more of the plurality of blade channels 302. The cutting blade 201 is operably coupled to a channel selection assembly 310 that includes an actuator 312 (FIG. 1) and a moving assembly 314 operably coupled to the actuator 312. As best shown in FIG. 1, the actuator 312 may be operably coupled to the housing 20.

Referring again to FIG. 6, the moving assembly 314 includes a drive assembly 316 and a blade mover 318. The drive assembly 316 is operably connected to the actuator 312 on the proximal end thereof and operably connected to the blade mover 318 on the distal end thereof. The channel selection assembly 310 is operable to selectively position the cutting blade 201 relative to each of the blade channels 302. Specifically, the moving assembly 314, via the blade mover 318, aligns the cutting blade 201 relative to one of the blade channels 302 upon actuation of the actuator 312, which causes the drive assembly 316 to move the blade mover 318 to position the cutting blade 201 into alignment with one of the blade channels 302 so that the cutting blade 201 may be selectively translated through the respective blade channel 302 upon actuation of the trigger assembly 70.

In this particular embodiment, the blade mover 318 is operably coupled to the cutting blade 201 so that the blade mover 318 moves the entire cutting blade 201 laterally across the end effector assembly 100 so that the cutting blade 201 may be selectively longitudinally aligned with each of the blade channels 302a, 302b, 302c. The blade mover 318, driven by the drive assembly 316, is positionable between extended and retracted positions. In the extended position, the cutting blade 201 is aligned with blade channel 302a. In the retracted position, the cutting blade 201 is aligned with blade channel 302c. In an intermediate position between the extended and retracted positions, the cutting blade 201 is aligned with blade channel 302b. However, the cutting blade 201 may be coupled to the blade mover 318 in any suitable arrangement so that the cutting blade 201 can be aligned with any of the channels 302 in any of the extended, retracted, or intermediate positions. As illustrated in FIG. 6A, the cutting blade 201 may include a channel 202 within which the blade mover 318 is seated so that the cutting blade 201 can longitudinally translate without being inhibited by the blade mover 318.

Figure 7:
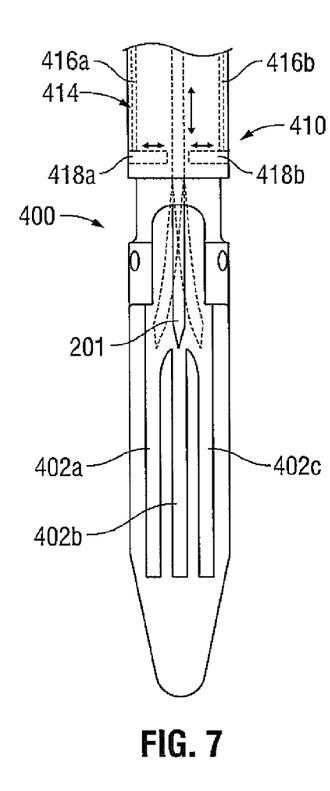
FIG. 7 is an enlarged, top plan view of the bottom jaw of one of the presently disclosed end effectors showing another embodiment of the presently disclosed knife assemblies in accordance with the present disclosure.

Another embodiment of a knife assembly is referred to generally as 400 and is illustrated in FIG. 7. Knife assembly 400 is similar to knife assembly 300 and is described herein only to the extent necessary to describe the differences in construction and operation. The knife assembly 400 defines a plurality of blade channels 402, in particular, first, second, and third blade channels 402a, 402b, 402c. The cutting blade 201 is positioned to selectively translate through one or more of the plurality of blade channels 402. The cutting blade 201 is operably coupled to a channel selection assembly 410 that includes the actuator 312 (FIG. 1) and a moving assembly 414 operably coupled to the actuator 312. The moving assembly 414 includes a first drive assembly 416a, a second drive assembly 416b, a first blade mover 418a, and a second blade mover 418b. The first drive assembly 416a is operably coupled to the first blade mover 418a and the second drive assembly 416b is operably coupled to the second blade mover 418b. The channel selection assembly 410 is operable to selectively position the cutting blade 201 relative to each of the blade channels 402. Specifically, the moving assembly 414 aligns the cutting blade 201 relative to one of the blade channels 402 upon actuation of the actuator 312 so that the cutting blade 201 may be selectively translated through the respective blade channel 402.

In this particular embodiment, the blade movers 418a and 418b each move laterally in reciprocal relation to one another along the end effector assembly 100 between extended and retracted positions so that the blade movers 418a and 418b can bend the cutting blade 201 in order to align the cutting blade 201 with each of the blade channels 402a, 402b, 402c. (For purposes of clarity, the bending of the cutting blade 201 has been exaggerated for illustrative purposes.) For example, when the blade mover 418a is in the extended position, the blade mover 418b is in the retracted position so that the blade mover 418a engages the cutting blade 201 as the cutting blade 201 distally translates, bending the cutting blade 201 into alignment with blade channel 402c. When the blade mover 418a is in the retracted position, the blade mover 418b is in the extended position so that the blade mover 418b engages the cutting blade 201 as the cutting blade 201 distally translates, bending the cutting blade 201 into alignment with blade channel 402a. Indeed, when the blade movers 418a and 418b are positioned in an intermediate position between extended and retracted positions, the cutting blade 201 remains longitudinally aligned with blade channel 402b as cutting blade 201 distally translates. However, the cutting blade 201 may be positioned relative to the blade movers 418a and 418b in any suitable arrangement so that the cutting blade 201 can be aligned with any of the blade channels 402 in any of the extended, retracted, or intermediate positions.

Figure 8:
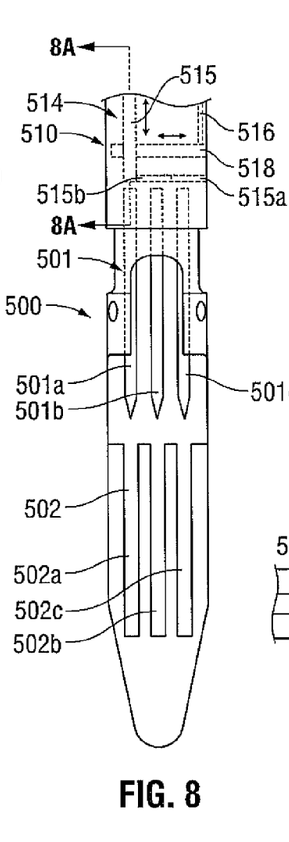
FIG. 8 is an enlarged, top plan view of the bottom jaw of one of the presently disclosed end effectors showing yet another embodiment of the presently disclosed knife assemblies in accordance with the present disclosure.

Another embodiment of a knife assembly is referred to generally as 500 and is illustrated in FIG. 8. Knife assembly 500 is similar to knife assembly 300 and is described herein only to the extent necessary to describe the differences in construction and operation. The knife assembly 500 defines a plurality of blade channels 502, in particular, first, second, and third blade channels 502a, 502b, 502c. The knife assembly 500 includes a plurality of cutting blades 501 positioned to selectively translate through one or more of the plurality of blade channels 502. As shown in FIG. 8, the knife assembly 500 may include first, second, and third cutting blades 501a, 501b, and 501c. The cutting blades 501 are operably coupled to a channel selection assembly 510 that includes the actuator 312 (FIG. 1) and a moving assembly 514 operably coupled to the actuator 312. The moving assembly 514 includes a drive assembly 516 and a pusher mover 518 operably coupled to a pusher 515. The pusher 515 is operably coupled to the trigger assembly 70 and actuable to distally translate upon actuation of the trigger assembly 70. The channel selection assembly 510 is operable to selectively laterally position the pusher 515 relative to each of the cutting blades 501. Specifically, the moving assembly 514 aligns the pusher 515 relative to one of the cutting blades 502 upon actuation of the actuator 312 so that the pusher 515 may be selectively translated upon actuation of the trigger assembly 70 to push one of the cutting blades 501 through the respective blade channel 502.

Figure 8A:
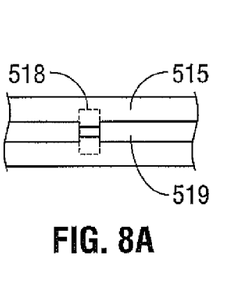
FIG. 8A is a partial, cross-sectional view of the indicated area of detail delineated in FIG. 8.

In this particular embodiment, the pusher mover 518 is operably coupled to the pusher 515 so that the pusher mover 518 moves the entire pusher 515 laterally across the end effector assembly 100 so that the pusher 515 may be longitudinally aligned with each of the cutting blades 501. The pusher mover 518, driven by the drive assembly 516 upon actuation of the actuator 312, is positionable between extended and retracted positions. In the extended position, the pusher 515 is aligned with cutting blade 501a and blade channel 502a. In the retracted position, the pusher 515 is aligned with cutting blade 501c and blade channel 502c. In an intermediate position between the extended and retracted positions, the pusher 515 is aligned with cutting blade 501b and blade channel 502b. However, the pusher 515 may be coupled to the pusher mover 518 in any suitable arrangement so that the pusher 515 can be aligned with any of the cutting blades 501 in any of the extended, retracted, or intermediate positions. The pusher 515 may also include one or more extensions 515a, 515b that enable the pusher 515 to engage and distally translate any two or more of the cutting blades 501 simultaneously so that the cutting blades 501 are simultaneously deployable when the pusher 515 is axially translated upon actuation of the trigger assembly 70. As illustrated in FIG. 8A, the pusher 515 may include a channel 519 defined therein and within which the pusher mover 518 is seated so that the pusher 515 can longitudinally translate without being inhibited by the pusher mover 518. In this manner, the pusher 515 engages the respective cutting blade 501 and distally translates the respective cutting blade 501 along the respective blade channel 502.

In some embodiments, the pusher 515 and/or one or more extensions 515a, 515b are couplable with the one or more cutting blades 501a, 501b, 501c via any suitable mechanical, electrical, and/or chemical coupling known in the art. For example, the pusher 515, the one or more extensions 515a, 515b, and/or the one or more cutting blades 501a, 501b, 501c may include any number of magnets, hook and loop-type fasteners, adhesives, etc. that facilitate the coupling of these features together. In this respect, the pusher 515 and/or one or more extensions 515a, 515b may draw the one or more cutting blades 501a, 501b, 501c proximally after distally translating the one or more cutting blades 501a, 501b, 501c along one or more of the respective blade channels 502.

Figure 9A:
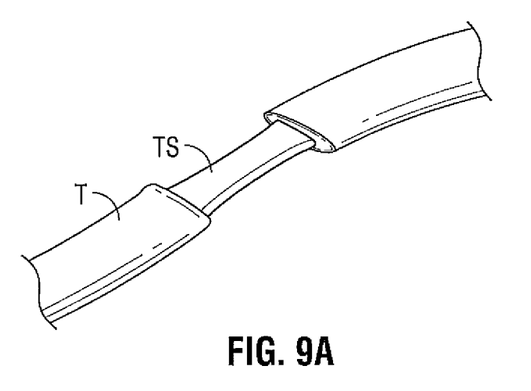
FIG. 9A is a perspective view of tissue after being sealed by one of the presently disclosed end effectors.
Figure 9B:
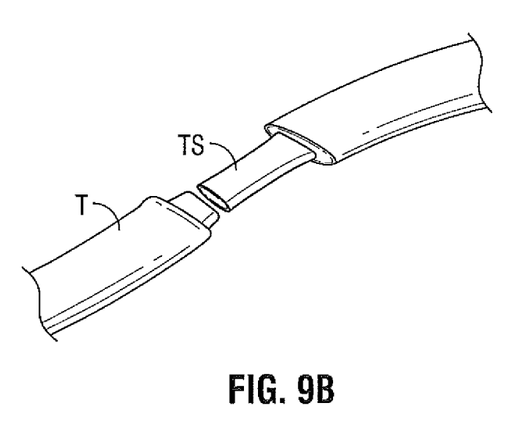
FIG. 9B is a perspective view of the tissue illustrated in FIG. 9A after being cut by one of the presently disclosed knife assemblies along a first blade channel thereof.
Figure 9C:
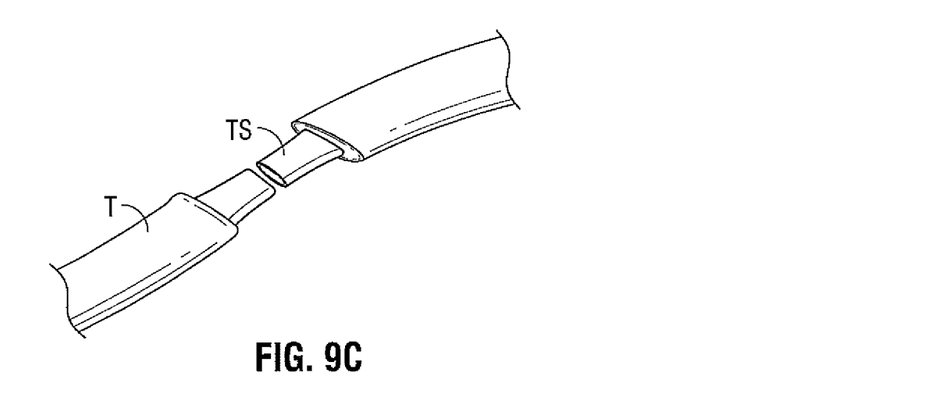
FIG. 9C is a perspective view of the tissue illustrated in FIG. 9A after being cut by one of the presently disclosed knife assemblies along a second blade channel thereof.
Figure 9D:
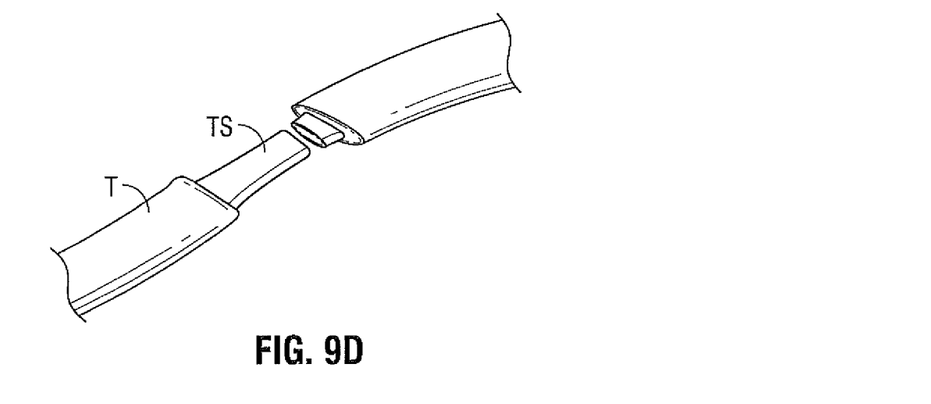
FIG. 9D is a perspective view of the tissue illustrated in FIG. 9A after being cut by one of the presently disclosed knife assemblies along a third blade channel thereof.
Figure 9E:
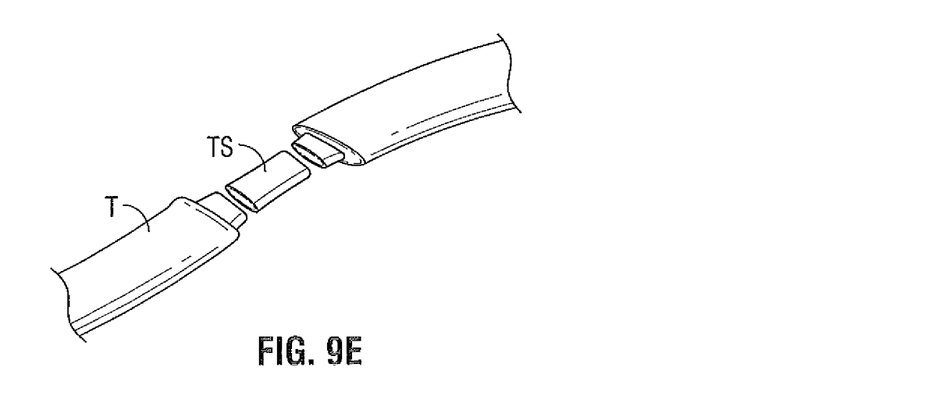
FIG. 9E is a perspective view of the tissue illustrated in FIG. 9A after being cut by one of the presently disclosed knife assemblies along the first and third blade channels thereof.

In operation, tissue is grasped between the jaws of one of the presently disclosed end effectors to form a tissue seal "TS" and to enable cutting of the tissue "T" (FIG. 9A). After the tissue "T" is sealed, the one or more cutting blades of one the presently disclosed knife assemblies are then positioned relative to the two or more blade channels of one of the presently disclosed knife assemblies. The one or more cutting blades are then moved through one or more of the two or more blade channels so that the tissue is cut with the one or more cutting blades along one or more of the two or more blade channels (FIGS. 9B-9E).

In some embodiments, an indicator may be disposed on the housing to let a user know into which channel(s) the blade(s) is(are) being deployed. The indicator may provide one or more visual, audible, and/or tactile indications for one or more of the channels and/or blades.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. A forceps, comprising:
   at least one shaft that includes an end effector assembly at a distal end thereof, the end effector assembly having a pair of jaw members selectively positionable relative to one another about a pivot, at least one of the jaw members including an electrically conductive tissue engaging surface adapted to connect to an electrosurgical energy source and at least one of the jaw members including at least two blade channels defined therein and extending therealong; and
   at least one cutting blade selectively positionable and translatable within at least one of the at least two blade channels.

2. The forceps according to claim 1, wherein at least one of the blade channels is positioned offset from a longitudinal axis defined through the center of the end effector assembly.

3. The forceps according to claim 2, wherein a wide seal zone is defined along the tissue engaging surface adjacent the at least one offset blade channel.

4. The forceps according to claim 1, wherein at least one of the blade channels is longitudinally aligned with a longitudinal axis defined through the center of the end effector assembly.

5. The forceps according to claim 1, further comprising at least two cutting blades.

6. The forceps according to claim 5, wherein the at least two cutting blades are sequentially deployable.

7. The forceps according to claim 5, wherein the at least two cutting blades are simultaneously deployable.

8. The forceps according to claim 1, further comprising a channel selection assembly, the channel selection assembly operable to selectively position the at least one cutting blade relative to at least one of the at least two blade channels.

9. The forceps according to claim 8, wherein the channel selection assembly includes an actuator having a moving assembly operably coupled thereto, wherein the moving assembly is configured to position the at least one cutting blade relative to at least one of the at least two blade channels upon actuation of the actuator.

10. The forceps according to claim 9, wherein the moving assembly includes at least one blade mover that is movable between extended and retracted positions, wherein the at least one blade mover is configured to position the at least one cutting blade relative to at least one of the at least two blade channels as the at least one blade mover moves between the extended and retracted positions.

11. The forceps according to claim 10, wherein the moving assembly includes at least two blade movers wherein each blade mover is adapted to move between extended and retracted positions.

12. The forceps according to claim 11, wherein the at least two blade movers are adapted to move in reciprocal relation relative to one another.

13. The forceps according to claim 10, wherein when the at least one blade mover is in the extended position, the at least one blade mover is positioned to engage the at least one cutting blade so that the at least one cutting blade is positioned in alignment with at least one of the at least two blade channels, at least one of the at least two blade channels positioned offset from the longitudinal axis.

14. The forceps according to claim 10, wherein the at least one blade mover is adapted to bend the at least one cutting blade into alignment with at least one of the at least two blade channels when the at least one blade mover moves between the retracted and extended positions.

15. The forceps according to claim 10, wherein the at least one blade mover is adapted to move the entirety of the at least one cutting blade laterally into alignment with at least one of the at least two blade channels as the at least one blade mover moves between the extended and retracted positions.

16. The forceps according to claim 1, further comprising at least two cutting blades and a moving assembly, each cutting blade aligned with at least one of the at least two blade channels, the moving assembly including a pusher, a pusher mover, and an actuator, wherein the pusher mover is adapted to align the pusher with at least one of the cutting blades upon actuation of the actuator.

17. The forceps according to claim 1, wherein axial translation of the pusher moves at least one of the cutting blades along at least one of the blade channels.

18. A method of cutting tissue grasped between the jaw members of an end effector of a forceps having at least one cutting blade, the end effector including a pair of jaw members, one of the pair of jaw members including at least two blade channels defined therein and extending therealong, the method comprising the steps of:
  positioning the at least one cutting blade relative to one of the at least two blade channels;
  moving the at least one cutting blade through at least one of the at least two blade channels; and
  cutting tissue with the at least one cutting blade along at least one of the at least two blade channels.

19. The method of claim 18, wherein the end effector defines a longitudinal axis that extends distally therethrough, and wherein positioning the at least one cutting blade relative to one of the at least two blade channels includes positioning the at least one cutting blade in a first one of the at least two blade channels so that the at least one cutting blade is disposed laterally adjacent to a second one of the at least two blade channels.

20. A surgical instrument, comprising:
  a housing having at least one shaft extending therefrom, the at least one shaft including an end effector assembly at a distal end thereof, the end effector assembly having a pair of jaw members selectively positionable relative to one another about a pivot, at least one of the jaw members including an electrically conductive tissue engaging surface adapted to connect to an electrosurgical energy source and at least one of the jaw members including at least two blade channels defined therein and extending therealong; and
  at least one cutting blade selectively positionable and translatable within at least one of the at least two blade channels.

* * * * *